United States Patent [19]

Kane

[11] 4,277,322

[45] Jul. 7, 1981

[54] OXYGEN SENSOR

[75] Inventor: William T. Kane, Big Flats, N.Y.

[73] Assignee: Corning Glass Works, Corning, N.Y.

[21] Appl. No.: 118,480

[22] Filed: Feb. 4, 1980

[51] Int. Cl.³ .......................................... G01N 27/58
[52] U.S. Cl. .............................................. 204/195 S
[58] Field of Search ............................ 204/1 S, 195 S

[56] References Cited

U.S. PATENT DOCUMENTS

| | | |
|---|---|---|
| 3,645,875 | 2/1972 | Record et al. .................. 204/195 S |
| 3,819,500 | 6/1974 | Van Esdonk et al. ........... 204/195 S |
| 3,935,089 | 1/1976 | Togawa et al. ................. 204/195 S |
| 3,978,006 | 8/1976 | Topp et al. ..................... 204/195 S |
| 4,021,326 | 5/1977 | Pollner et al. .................. 204/195 S |
| 4,080,276 | 3/1978 | Bode .............................. 204/195 S |
| 4,097,353 | 6/1978 | Kishida et al. ................. 204/195 S |
| 4,101,404 | 7/1978 | Blumenthal et al. ........... 204/195 S |
| 4,121,988 | 10/1978 | Sano et al. ..................... 204/195 S |
| 4,121,989 | 10/1978 | Shum et al. .................... 204/195 S |
| 4,126,532 | 11/1978 | Takao et al. .................... 204/195 S |
| 4,140,611 | 2/1979 | Yaegashi et al. ................ 204/195 S |
| 4,164,462 | 8/1979 | Ichikawa et al. ............... 204/195 S |
| 4,198,279 | 4/1980 | Brown et al. ................... 204/195 S |

FOREIGN PATENT DOCUMENTS

| | | |
|---|---|---|
| 2351815 | 4/1975 | Fed. Rep. of Germany ....... 204/195 S |
| 2738882 | 3/1978 | Fed. Rep. of Germany ....... 204/195 S |
| 53-29188 | 3/1978 | Japan ................................. 204/195 S |

OTHER PUBLICATIONS

English language abstract of Japanese Laid-open Patent application publication 54-10792.

R.G.H. Record, reprint from Instrument Practice, Mar., 1970, published in Great Britain.

R.G.H. Record, reprint from Metallurgia and Metal Forming, Dec. 1972/Jan. 1973, published in Great Britain.

*Primary Examiner*—G. L. Kaplan
*Attorney, Agent, or Firm*—Richard N. Wardell

[57] ABSTRACT

A metal film electrode on the outer surface of an electroded, oxygen-ion-conducting solid electrolyte, closed end portion of an oxygen sensor tube is maintained in contact with the electrolyte and in its electrical conducting function by a compressible, porous, ceramic boot firmly press-fit onto and over the electroded end portion in slidable and frictional engagement with the outer film electrode (including any connector or reinforcing wire therein or thereon). Boot has open porosity of greater than 50 (or 80) volume percent and can consist essentially of zirconia, such as a sintered mass of zirconia fibers.

10 Claims, 4 Drawing Figures

OXYGEN SENSOR

CROSS-REFERENCE TO RELATED APPLICATION

U.S. application Ser. No. 118,479 of William T. Kane and William P. Whitney entitled FURNACE AND METHOD WITH SENSOR, filed on the same date and assigned to the same assignee as was the present application, discloses and claims the invention pertaining to the getter 50 disclosed herein.

BACKGROUND OF THE INVENTION

This invention relates to an improvement in the known type of oxygen sensor comprising a solid oxygen-ion-conducting electrolyte with porous, thin layer or film, metal (e.g. platinum) electrodes attached on substantially opposite surfaces of the electrolyte. When each electrode of this type of sensor is in contact with a different oxygen concentration and the electrodes are connected in an electrical measuring circuit, oxygen ions migrate through the electrolyte between the electrodes coincidently with a flow of electrons in the circuit generating a measurable voltage or electromotive force between (or across) the electrodes or two points in the circuit.

This type of sensor has been known for use in monitoring: (1) exhaust gases of internal combustion engines in thermodynamic nonequilibrium for control of the air-fuel ratio in the combustion process, (2) stack or flue gases of industrial combustion furnaces for control of the combustion process to eliminate smoke and other undesirable emissions, and (3) furnace atmospheres of metal heat treating and other furnaces in substantial thermodynamic equilibrium for control of their oxygen potential, e.g. in nonoxidizing and reducing gas atmospheres.

However, durability of the thin layer or film metal electrode in contact with the monitored flowing hot gases has been a problem. Such electrode has been variously noted to be adversely affected by thermal shock and differential expansion stresses in the sensor, mechanical abrasion and impact stresses caused by particles carried in the flowing gases, and chemical reaction effects with constituents in the gases being monitored.

In U.S. Pat. No. 3,645,875, it is noted that reducing gas atmospheres and metal vapors in such atmospheres of metal heat treating furnaces cause embrittlement of platinum film electrodes and adversely affect the bond between such electrode and the solid electrolyte. The remedy suggested in this patent for such problems is adherently attaching a thin, porous, protective overlayer on the platinum film electrode and on the adjacent electrolyte surface not covered by the electrode so as to secure the electrode on the electrolyte. Such adherent overlayer is applied by firing a paste coating or flame spraying a coating of the overlayer on the electrode and electrolyte surfaces.

A similar remedy is shown in U.S. Pat. Nos. 3,978,006, 4,021,326 and 4,126,532 to protect a catalytic metal film electrode on a sensor against mechanical and chemical damage in internal combustion engine exhaust gases. Additional application techniques noted therein include plasma spraying, metal plating followed by oxidation and various other thin-layer techniques such as thermal vaporizing, precipitation from gases and reactive vapor deposition.

Other examples of thin, porous coatings similarly adherently applied only onto platinum film electrodes of sensors, mostly for internal combustion engines, are shown in U.S. Pat. Nos. 3,935,089, 4,080,276, 4,097,353 and 4,164,462, and in Japanese laid-open patent application publication No. 54-10792. However, U.S. Pat. No. 4,164,462 notes that some of such adherent, porous overlayers or coatings can suffer a durability problem (cracking) of their own. This latter fact was confirmed in my studies, which showed that such overlayers (e.g. of alumina cement) readily crack and spall off, thereby leaving significant portions of the metal film electrode uncovered. A consequence of such results is that embrittled and loosened metal film electrodes can crack and flake off or separate from the electrolyte causing early failure of the sensor.

Trying to improve the strength and adherence of the overlayer by firing it on the sensor at higher temperatures above about 1150° C. is often unsatisfactory, especially for sensors with stabilized zirconia electrolytes to be used in metal heat treating processes. Besides the possibility of destroying the needed porosity by sintering the overlayer too dense, reheating of the stabilized zirconia electrolyte (while firing the overlayer) above about 1150° C. causes a change in the zirconia structure, which in turn causes the electrolyte to exhibit sluggish, nonideal behavior in service at temperatures below about 1150° C. as is often the case in metal heat treating processes.

Another effort to overcome the metal film electrode adherence problem in sensors for automotive exhaust gas is shown in Japanese laid-open patent application publication No. 53-29188. This effort involved leaving holes in the electrode with exposed electrolyte surface being covered, along with the electrode, with a porous thin layer of inorganic compound to prevent stripping and scattering of the electrode.

Although not concerned with a problem of keeping metal film electrodes adhered to a solid electrolyte surface, U.S. Pat. No. 4,121,989 shows a specially tailored oxygen sensor device for greater efficiency, accuracy and reproducible operation in monitoring stack gases from industrial combustion furnaces. Such device has felted ceramic fiber discs partly embedded into wet electrode paste of coatings and fired therein. Then chloroplatinic acid is applied through the felted discs and thermally reduced to platinum particles dispersed over the electrode surfaces and within the felted discs to augment the capacity of the platinum electrodes to effect the ionization-deionization reactions of oxygen in the device.

SUMMARY OF THE INVENTION

This invention is premised upon my recognition and discovery that it is not necessary to suffer the burdensome and not infrequently fruitless techniques, as have apparently consistently been the prior art practices and many times requiring undesirable reheating of the solid electrolyte, of applying adherent, thin-layer, porous, inorganic coatings on and over metal film electrodes on the outer surface of solid electrolyte at and near the closed end of an oxygen sensor tube in order to secure contact of that electrode with the electrolyte and maintain electrical conducting integrity of that electrode. Accordingly, I have recognized and discovered a much simpler and reliable (as well as easily renewable) way of providing assured maintenance of contact between such electrode and the electrolyte and of electrical conducting ability in the electrode. That way involves the firm press-fitting of a compressible, porous, ceramic boot onto and over the electroded end portion of the sensor tube in slidable and frictional engagement with the outer film electrodes thereof (including any connector or reinforcing wire therein or thereon) so as to maintain the contact between the electrolyte and that electrode, and to maintain the electrical conducting function of that electrode, for extended periods of sensor life - despite any embrittling or cracking effects caused in that electrode film by service conditions to which it is subjected. Thus, the boot simply physically prevents spalling of flakes or particles of the outer metal film electrode off of the electrolyte.

In a more precise manner, the invention is defined as an oxygen sensor comprising:

a tubular body having a closed end and an opposite open end, an electroded portion of the body including the closed end and comprising a solid oxygen-ion-conducting electrolyte with metal film electrodes attached on the outer and inner surfaces of the electrolyte, a compressible, porous, ceramic boot firmly press-fit onto and over the electroded portion in slidable and frictional engagement with the electrode on the outer surface of the electrolyte so as to maintain contact between the electrolyte and the electrode on the outer surface of the electrolyte and to maintain the electrical conducting function of that electrode, and the ceramic of the boot being thermodynamically stable in the atmosphere to which it is to be subjected and nonreactive with the metal electrode in contact with the boot.

This invention also includes the oxygen sensor device as described herein comprising the combination of a casing, sensor tube having an electroded end portion with platinum group metal film electrodes on an oxygen-ion-conducting electrolyte, the noted boot on and over the outer electrode, and a platinum group metal contaminant getter consisting essentially of the same platinum group metal as in the outer electrode.

DETAILED DESCRIPTION

Figure 1:
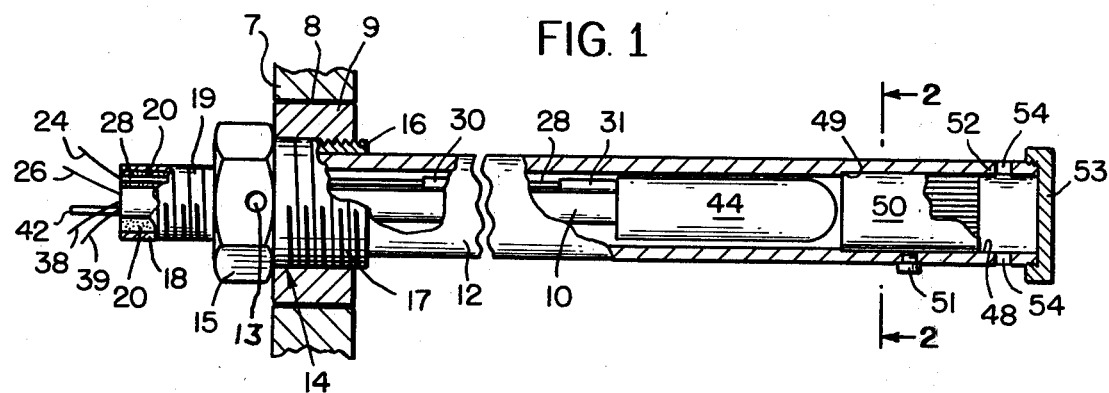
FIG. 1 is a partially sectioned view of a portion of a heat treating furnace enclosure or wall through which is mounted an oxygen sensor device of the present invention.

FIG. 1, furnace wall 7 defines (in part) the furnace chamber space to the right of such wall. Mounted in an opening in the wall 7, as by welded joint 8, is a collar member 9, whose inner annular surface is threaded in a complementary manner to receive the threads 17 on the larger end portion 16 of the fitting 14 for mounting the oxygen sensor device in and through the wall 7.

The oxygen sensor device comprises an oxygen-ion-conducting solid electrolyte tube 10 positioned inside a protective casing 12. In the preferred embodiment, the solid electrolyte is a yttria-stabilized zirconia containing about 8% $Y_2O_3$ by weight, and casing 12 is made of Inconel alloy. However, any solid oxygen-ion-conducting electrolyte and any suitable heat-resistance metal of the casing can be used. One end of casing 12 is positioned inside the larger bore of fitting 14 so as to fully extend into that bore passing through larger end portion 16 and partly into the hexagonal-shaped middle portion 15 of fitting 14. Three set screws 13 (only one shown), equally spaced around middle portion 15, hold the casing 12 within fitting 14; however, other fastening means can be employed as desired. Screws 13 and fitting 14 are preferably made of stainless steel. Fitting 14 includes a smaller end portion 18 with threads 19 for connection to a terminal structure such as a conventional thermocouple head (not shown). Smaller end portion 18 also has a bore centrally within which the open end of electrolyte tube 10 is fastened by means of a suitable cement 20, such as sauereisen cement.

Figure 2:
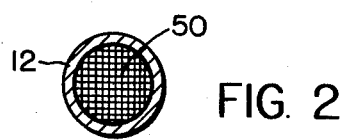
FIG. 2 is a sectional view taken along a line 2—2 in FIG. 1.
Figure 3:
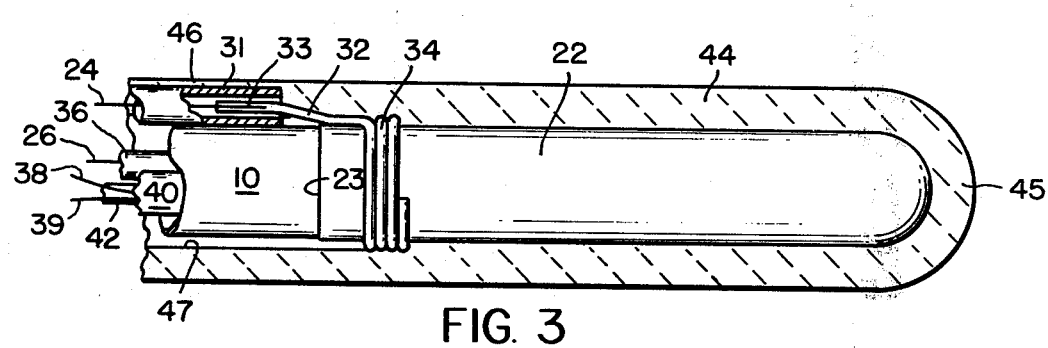
FIG. 3 is an enlarged sectional view of one variation of an oxygen sensor useful in the present invention.

As shown in FIGS. 2 and 3, the closed end of electrolyte tube 10 has an outer platinum film electrode 22 extending over the entire hemispherical end of the tube and on up the tube a short distance to the edge 23 of electrode 22. An inner platinum film electrode (not shown) extends over the portion of the inner bore surface of the tube 10 opposite to that of the outer surface covered by electrode 22 (as in conventional). The platinum film electrodes can be formed by any suitable method, but it is preferred to use a platinum paste which is painted on the desired surfaces and then fired thereon to partially sinter the resulting platinum coating. A particularly desired paste mixture comprises equal parts by weight of platinum resinate paste containing 65.5 wt.% Pt and platinum dust or powder of −325 mesh U.S. Standard Screen, and to 85 parts by weight of which is added 15 parts by weight of lavender oil for providing a paint consistency to the paste mixture. This mixture is applied to a cleaned electrolyte tube surface, dried at about 120° C. for 15 minutes and then fired at about 1150° C. for one hour. This procedure is used for each coating application and usually three coating applications, one on top of the other, are necessary for an adequate thickness of platinum to form the film electrodes. The second and subsequent coatings are usually fired at about 1000° C. for one hour.

By any suitable or conventional means, an outer platinum electrical lead wire 24 is connected to outer electrode 22 and an inner platinum electrical lead wire 26 is connected to the inner electrode (not shown). Typically such wires can be of 12-17 mil diameter sizes. Wire 24 is carried within a single-bore alumina tube 28 extending through casing 12 and fitting 14 to the left end of portion 18. Such tube 28 is also fastened within the bore of portion 18 by means of the cement 20. To accommodate the differing thermal expansions of electrolyte tube 10 and alumina tube 28 while still being above to hold tube 28 to tube 10, short, single-bore, alumina sleeves 30,31 are cemented to tube 10 as shown in FIGS. 1-3 and the tube 28 is slidably held within the bore of sleeves 30,31. Thus tube 28 electrically insulates and physically protects wire 24 without causing any differential thermal expansion stresses in the sensor device.

Figure 4:
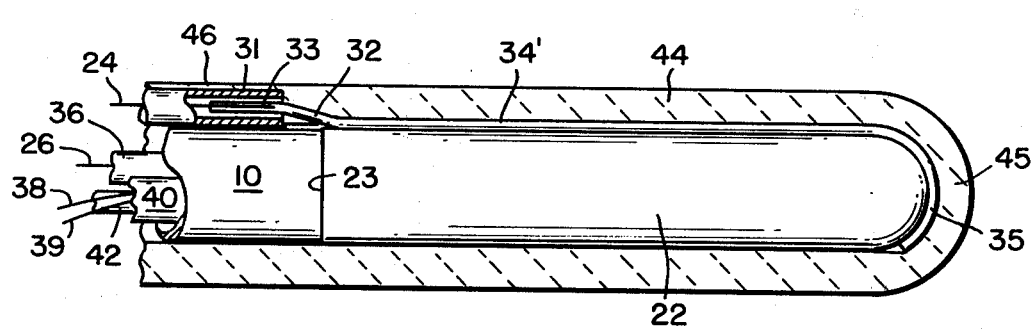
FIG. 4 is an enlarged sectional view of another variation of an oxygen sensor useful in the present invention.

In the preferred embodiment, a platinum connector wire 32 (see FIGS. 2 and 3) is fixed to electrode 22 and spot welded to wire 24 at their overlap junction 33. Wire 32 is preferably thicker than wire 24, e.g. 17-40 mil diameter. In connecting wire 32 to electrode 22, only one fired paste mixture coating is made prior to placing wire 32 on that coating. Wire 32 can be placed on the initial electrode coating in any desired manner, e.g. by coiling a portion 34 around the electrode coating 22 as in FIG. 3 or by molding a portion 34' to extend longitudinally along electrode coating 22 and around its hemispherical end with curved portion 35 of wire 32 as in FIG. 4. After wire 32 is so placed on the intial coating of electrode 22, two additional fired paste mixture coatings are applied over the initial electrode coating 22 and the portions of wire 32 laid thereon. Those fired top coatings of electrode 22 serve to fasten or bond wire 32 to electrode 22 in the position in which it was placed thereon.

Inner lead wire 26 is carried in a single-bore alumina tube 36 from adjacent the inside hemispherical closed end surface of tube 10 (where a small protruding portion of wire 26 is fastened to the inner electrode by any suitable or conventional means) on through the bore of tube 10 to the opposite end thereof.

Also extending through the bore of tube 10 are thermocouple wires 38,39 carried in a double-bore alumina tube 40 and a tube 42 for a reference oxygen gas (e.g. air). These components extend into the bore of tube 10 to a point shortly beyond electrode edge 23 (i.e. between edge 23 and the hemispherical closed end of tube 10). It is in the vicinity of that point at which the thermocouple wires protrude out of tube 40 and are joined in a thermocouple junction and also the reference gas is introduced to the inner electrode from the open end of tube 42. Likewise, these components also extend oppositely to the other end of tube 10, where further extensions of wires 38,39 and tube 42 as well as of wires 24,26 are available for respective appropriate connections to a thermocouple temperature measuring circuit, a gas supply and a voltage measuring circuit, all as is conventional. In order to insure the physical integrity of the components extending within tube 10, it is preferred to cement the ends of tubes 36, 40, 42 within the end of tube 10 fastened in the bore of fitting portion 18; however, care is taken to make sure that the cement does not completely seal the open end of tube 10 so that the reference gas is allowed to exit therefrom.

The main improvement element of the present invention is preferably embodied in a porous ceramic boot 44. It is advantageous to slidably and frictionally engage the compressible, porous, ceramic boot or cover 44 and its hemispherically closed end 45 onto and over electrode 22 and wire 32 to physically hold the electrode 22 and wire 32 in contact with electrolyte 10 even if the platinum of electrode 22 and wire 32 becomes embrittled after an extended period of service and would otherwise tend to separate from contact with the electrolyte tube 10. Boot 44 is made of a sintered, porous, oxide that is thermodynamically stable in the non-oxidizing or reducing atmosphere of the heat treating furnace and is nonreactive with platinum. Preferably such oxide is zirconia which is advantageously in a stabilized form with a stabilizer that is also nonreactive with platinum. Desirably it is yttria-stabilized zirconia with 8 wt.% $Y_2O_3$. The boot 44 should have an open porosity of greater than 50 volume % (preferably greater than 80 volume %) for adequate rapid passage of monitored atmosphere to the electrode 22. In the preferred embodiment, boot 44 is composed of a sintered mass of short 8 wt.% yttria-stabilized zirconia fibers (e.g. 1/16 inch mean length and 4–6 microns diameter) mixed with a minor portion (about 1 wt.%) of submicron zirconia powder stabilized with a similar percentage of yttria. Such mixture is shaped as a boot 44 and fired sufficiently to render the sintered boot to be a coherent, substantially firm structure with over 80 vol. % open porosity and yet capable of being grooved or compressed with the manual pressure of a person's fingernail. Thus, such boot 44 can be slidably and firmly press-fit onto tube 10 over electrode 22 and wire 32 whereby the sliding engagement with wire 32 easily grooves or compresses an inner portion of boot 44 just sufficient to accommodate wire 32 therein without otherwise damaging boot 44. It is also advantageous for the boot 44 to extend over the tip of sleeve 31 so as to protect the portion of wire 32 entering sleeve 31. The latter is easily accommodated by sleeve 31 further grooving or compressing the inside of portion 46 of boot 44 just sufficient to accommodate sleeve 31, again without otherwise damaging boot 44. In the case of wire coil 34 (FIG. 3), it compresses the inner diameter 47 of boot 44 to an enlarged size just sufficient to accommodate coil 34.

As noted in the aforementioned copending U.S. application Ser. No. 118,479, it is advantageous to employ a getter 50 upstream from the electroded portion of tube 10. Accordingly in my present invention, I preferably include a honeycomb getter 50 positioned within the portion of casing 12 having a bore 48 of enlarged diameter relative to the remainder of casing 12 whereby the getter 50 is further positioned by shoulder 49 joining the two bore diameters of casing 12. Stainless steel set screw 51 engages and holds getter 50 in its position. Getter 50 comprises a thin-walled honeycomb body with a plurality of passages therethrough for passage of furnace atmosphere to the electroded portion of the oxygen sensor within boot 44. Such honeycomb body is known to cause relatively little back-pressure effect against incoming gases thereto, and that minor effect is easily overcome by the positive (i.e. greater than atmospheric) pressure and/or velocities of gas atmosphere flowing in a furnace chamber and entering the getter 50. Preferably the honeycomb getter 50 comprises a ceramic honeycomb body with porous walls containing platinum thereon and desirably within the open pores in the walls. Such honeycomb body can be made by any suitable or known method, such as those described in U.S. Pat. Nos. 3,112,184 and 3,790,654, especially that of the latter patent. Such body can have transverse passage or cell density ranging from about 15 to 900 cells/square inch of transverse cross-section, but preferably of 300 cells/in$^2$. The wall thicknesses can range from about 2 to 50 mils, but preferably is about 10 mils. Wall open porosity is advantageously in the range of 10 to 50 volume %, but preferably at least about 14 vol. %. The ceramic forming the body should be reasonably thermodynamically and physically stable under conditions of hot furnace nonoxidizing atmospheres passing therethrough. Preferably the ceramic consists essentially of two crystal phases: zirconia and magnesium aluminate spinel. The preferred zirconia/spinel weight % ratios range from 65/35 to 30/70, with 60/40 being most preferred. The platinum can be applied to the walls of the honeycomb body in any suitable or known manner. Generally one can employ the conventional technique of impregnating the porous honeycomb body by dipping it in chloroplatinic acid (usually in an aqueous solution of 25 wt.% $H_2PtCl_6$), draining excess solution from gas atmosphere to thermally decompose and reduce the acid to platinum metal residue on the honeycomb body. This dip/fire procedure is repeated about three to four times or so as to obtain a platinum loading of at least about 5 wt.% (and preferably about 10 wt.%) of the platinized honeycomb body. Such platinized honeycomb body with a 2 inch length and a ⅝ inch diameter has been found quite adequate to provide getter protection for an electroded portion of an electrolyte having a 2 inch length and a ⅜" outside diameter.

Comparative tests in gas carburizing furnaces have shown that sensors like those described herein, but not including either boot 44 or getter 50 survived up to 9 weeks service before the sensors failed to properly function. Such sensors protected only with the getter 50 have survived up to more than 53 weeks—almost a 6 fold improvement in service life. The sensors containing the boot 44, but not protected by getter 50, survived up to more than 16 weeks service—a modest improvement despite lack of getter protection. In the case of the sensors protected with both the getter 50 and the boot 44, the survival period has not been well determined yet, but it has extended up to more than 33 weeks without failure (as the service test is continuing).

As is evident from the description herein, the honeycomb getter 50 is a consumable element easily replaced as needed to provide adequate gettering for continued or extended life of the sensor device.

Background information on the operation of oxygen sensors for monitoring oxygen potential in and controlling nonoxidizing or reducing atmospheres of carburizing and other metal heat treating furnaces can be found in the articles by R. G. H. Record in Instrument Practice, March 1970, and Metallurgia and Metal Forming, December 1972/January 1973, both published in Great Britain. These articles are incorporated herein by this reference.

As an option, casing 12 may include a protective extension 52 having a cap 53 threaded onto and closing its end opening, but also having side ports 54 for entrance of furnace atmosphere into casing 12. However, generally the extension 52 is omitted and end the casing 12 at the entrance (right) end of getter 50 with such casing end being open to the furnace atmosphere as an inlet therein. An optional outlet in the casing can be suitably provided and arranged at any point to the left of boot 44 (i.e. the electroded portion of tube 10) for exiting monitored atmosphere either within or outside of the furnace enclosure 7, e.g. by leaving an opening or passage through cement 20 within fitting portion 18 whereby the monitored furnace atmosphere passes completely through the casing 12 and fitting 14 to be suitably exited outside the furnace enclosure 7. However, for use in conventional steel carburizing furnaces wherein the furnace atmospheres are thoroughly circulated, by means of fans, at high velocities such as 200 feet per second, many experimental tests have shown there is no need for a separate outlet from the casing (i.e. separate from the inlet). Thus, the hurricane-like atmosphere condition in the carburizing furnace is sufficiently effective to continuously force new sequential portions of the atmosphere into the sensor device employed in this invention. Of course, the plurality of passages of honeycomb getter 50 and the high porosity of boot 44 facilitate easy access to the electroded portion of tube 10. The strong swirling action of the carburizing furnace atmosphere apparently causes turbulent flow in portions of such atmosphere in casing 12 so as to push them into contact with the electroded portion and then flush them back out of the inlet in order to allow new sequential portions to be pushed into casing 10 for contact with the electroded portion.

Thus, the method of using the above-described sensor involves the heat treatment of metal workpieces in the chamber to the right of wall 7, into which the sensor device protudes. Sequential portions of nonoxidizing or reducing furnace atmosphere enter the inlet at the right end of casing 12, e.g. the ports 54, and pass through getter 50. After removal of platinum contaminants from those portions of atmosphere by getter 50, the portions continue to flow to and through boot 44 into contact with the electroded portion of electrolyte tube 10 containing electrode 22, wherein the oxygen potential of such atmosphere portions are detected and monitored by the oxygen sensor. Thereafter, such atmosphere portions are flushed out of the casing 12. During this operation of the method, air as a preferred reference gas is flowed into the left end of tube 42, through that tube and into the closed end of the bore within tube 10 where the inner platinum film electrode is located. Thereafter, the air reference gas passes through the bore of tube 10 to exit from its partially open left end.

While the detailed examples have been described herein with illustrative reference to only platinum as getter and film electrode (including connector wire), it should be understood that any other platinum group metal (e.g. palladium, ruthenium, etc.) can be used as desired.

In the case of the oxygen sensor of this invention when employed without getter 50, the metal film electrode can be of any other suitable metal besides platinum group metals, e.g. gold, silver, etc.

What is claimed is:
1. An oxygen sensor comprising
   a tubular body having a closed end and an opposite open end,
   an electroded portion of the body including the closed end and comprising a solid oxygen-ion-conducting electrolyte with metal film electrodes attached on the outer and inner surfaces of the electrolyte,
   a compressible, porous, ceramic boot firmly press-fit onto and over the electroded portion in slidable and frictional engagement with the electrode on the outer surface of the electrolyte so as to maintain contact between the electrolyte and the electrode on the outer surface of the electrolyte and to maintain the electrical conducting function of that electrode, and
   the ceramic of the boot being nonreactive with the metal electrode in contact with the boot.
2. The sensor of claim 1 wherein the boot has an open porosity of greater than 50 volume percent.
3. The sensor of claim 1 wherein the ceramic of the boot consists essentially of zirconia.
4. The sensor of claim 1 wherein the boot consists essentially of a sintered mass of zirconia fibers.
5. The sensor of claim 4 wherein the boot has an open porosity of greater than 80 volume percent.
6. The sensor of claim 1 wherein the electrolyte is stabilized zirconia.
7. An oxygen sensor device comprising
   a casing having an inlet for entry thereinto of gas atmosphere to be monitored and which contains platinum group metal contaminants,
   an oxygen sensor within the casing and comprising a tubular body with an electroded portion and a compressible porous, ceramic boot,
   the tubular body having a closed end and an opposite open end,
   the electroded portion including the closed end and comprising a solid oxygen-ion-conducting electro- lyte with film electrodes of platinum group metal attached on the outer and inner surfaces of the electrolyte, the ceramic boot firmly press-fit onto and over the electroded portion in slidable and frictional engagement with the electrode on the outer surface of the electrolyte so as to maintain contact between the electrolyte and the electrode on the outer surface of the electrolyte and to maintain the electrical conducting function of that electrode, the ceramic of the boot being nonreactive with the platinum group metal electrode in contact with the boot, and a platinum group metal contaminant getter consisting essentially of the same platinum group metal as in the electrode on the outer surface of the electrolyte and arranged in the casing between the inlet and the electroded portion so that the atmosphere to be monitored passes into contact with the getter to effect gettering of the platinum group metal contaminants from the atmosphere.

8. The device of claim 7 wherein the getter comprises a thin-walled honeycomb body extending across the casing, having a plurality of passages arranged for the atmosphere to pass therethrough, and having the platinum group metal of the getter contained on the walls of the passages and exposed to the atmosphere passing therethrough.

9. The device of claim 7 wherein the boot has an open porosity of greater than 50 volume percent.

10. The device of claim 7 wherein the ceramic of the boot consists essentially of zirconia.

* * * * *

UNITED STATES PATENT AND TRADEMARK OFFICE
CERTIFICATE OF CORRECTION

PATENT NO. : 4,277,322

DATED : July 7, 1981

INVENTOR(S) : William T. Kane

It is certified that error appears in the above–identified patent and that said Letters Patent are hereby corrected as shown below:

Column 4, line 53, change "above" to -- able --.

Signed and Sealed this

Twentieth Day of October 1981

[SEAL]

Attest:

GERALD J. MOSSINGHOFF

Attesting Officer

Commissioner of Patents and Trademarks